US007382855B2

(12) United States Patent
Tani et al.

(10) Patent No.: US 7,382,855 B2
(45) Date of Patent: Jun. 3, 2008

(54) FLUORESCENT X-RAY ANALYSIS METHOD AND FLUORESCENT X-RAY ANALYSIS DEVICE

(75) Inventors: Yoshiyuki Tani, Osaka (JP); Hiroshi Iwamoto, Osaka (JP); Takao Hisazumi, Osaka (JP); Yukihiro Iwata, Osaka (JP); Etsuyoshi Sakaguchi, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/587,856

(22) PCT Filed: Apr. 27, 2005

(86) PCT No.: PCT/JP2005/007977

§ 371 (c)(1),
(2), (4) Date: Oct. 27, 2006

(87) PCT Pub. No.: WO2005/106440

PCT Pub. Date: Nov. 10, 2005

(65) Prior Publication Data

US 2007/0248211 A1 Oct. 25, 2007

(30) Foreign Application Priority Data

Apr. 28, 2004 (JP) ............................. 2004-133135
Nov. 2, 2004 (JP) ............................. 2004-318844

(51) Int. Cl.
*G01N 23/223* (2006.01)
(52) U.S. Cl. ...................................................... 378/44
(58) Field of Classification Search ............. 378/44–50
See application file for complete search history.

(56) References Cited

U.S. PATENT DOCUMENTS 5,570,406 A * 10/1996 Komatani .................... 378/44
6,118,844 A * 9/2000 Fischer ....................... 378/48

FOREIGN PATENT DOCUMENTS

| JP | 8-43329 | 2/1996 |
| JP | 2001-99795 | 4/2001 |
| WO | WO 02/31534 A2 | 4/2002 |

OTHER PUBLICATIONS

European Search Report, issued in Corresponding European Patent Application No. 05737192.4-2204, dated on Nov. 15, 2007.
Afshari et al. "Quantitative Measurement of Lead in Paint by XRF Analysis Without Manual Substrate Correction", Applied Radiation and Isotopes, vol. 48, No. 10-12, pp. 1425-1431, 1997.

* cited by examiner

Primary Examiner—Courtney Thomas
(74) Attorney, Agent, or Firm—McDermott Will & Emery LLP

(57) ABSTRACT

It is possible to solve the problem of the conventional fluorescent X-ray analysis that a concentration calculation result can be obtained only after elapse of a time set as a measurement time. In the fluorescent X-ray analysis method and fluorescent X-ray analysis device according to the present invention, a sample measurement condition is set before starting the measurement and the measurement concentration of the element contained in the sample and the measurement accuracy are calculated. When the measurement accuracy has become a value satisfying the predetermined measurement condition, the measurement is terminated and the concentration at that moment is outputted.

18 Claims, 11 Drawing Sheets

Fig.6

| Measured concentration | Measurement accuracy | Assessment | Action |
|---|---|---|---|
| ○ | ○ | ○ | pass |
| ○ | × | ? | high analysis accuracy required |
| × | ○ | × | return to part manufacturer |
| × | × | ? | high analysis accuracy required |

←—Tb1

| Measured concentration | X<Xt | Xt≦X |
|---|---|---|
| Determination | ○ | × |
| Measurement accuracy | σx<σt | σt≦σx |
| Determination | ○ | × |

Fig.8

| Measured concentration | Measurement accuracy | Assessment | Action |
|---|---|---|---|
| ○ | ○ | ○ | pass |
| ○ | △ | △ | test again |
| ○ | × | ? | high analysis accuracy required |
| △ | ○ | △ | discuss with part manufacturer |
| △ | △ | △ | test again |
| △ | × | ? | high analysis accuracy required |
| × | ○ | × | return to part manufacture |
| × | △ | △ | test again |
| × | × | ? | high analysis accuracy required |

←—Tb2

| Measured concentration | X≦Xt1 | Xt1<X≦Xt2 | Xt2<X |
|---|---|---|---|
| Determination | ○ | △ | × |
| Measurement accuracy | σx≦σt1 | σt1<σx≦σt2 | σt2<σx |
| Determination | ○ | △ | × |

FLUORESCENT X-RAY ANALYSIS METHOD AND FLUORESCENT X-RAY ANALYSIS DEVICE

RELATED APPLICATION

This application is a national phase of PCT/JP2005/007977 filed Apr. 27, 2005, which claims priority from Japanese Application No. 2004-133135 filed Apr. 28, 2004 and Japanese Application No. 2004-318844 filed Nov. 2, 2004, the disclosures of which Applications are incorporated by reference herein. The benefit of the filing and priority dates of the International and Japanese Applications is respectfully requested.

TECHNICAL FIELD

The present invention relates to a fluorescent X-ray analysis method and device, and more particularly is used in the detection of environmental hazardous substances that are admixed in parts used in electronic and electrical devices and made up of many different compositions.

BACKGROUND ART

The danger of environmental hazardous substances being contained in the parts that make up electronic and electrical devices has been indicated in recent years, and some countries or states are now regulating by law or ordinance the amounts in which these environmental hazardous substances can be contained. For instance, in the countries of the European Union, the RoHS directive (Restriction on the use of certain Hazardous Substances in electrical and electronic equipment) prohibits the use of parts containing cadmium (Cd), lead (Pb), mercury (Hg), polybrominated biphenyl (PBB), polybrominated diphenyl ether (PBDE), or hexavalent chromium (Cr(VI)) in an amount of equal to or more than 1000 ppm (100 ppm in the case of cadmium). Consequently, it is essential that manufacturers of electronic and electrical devices make sure the parts they produce do not contain environmental hazardous substances in amounts greater than allowed.

The most common way to measure the amounts in which elements are contained is to use a fluorescent X-ray analyzer that has a sensitivity of a few dozen parts per million and allows non-destructive measurement.

Procedures for using this type of analysis method to quantify the concentration of elements contained in a sample are generally well known. An example of the method of these procedures will be described through reference to FIG. 11 (see Patent Document 1).

In FIG. 11, first, in step 301, a measurement time t is set, after which measurement begins (see step 302). Then, measurement is carried out (see step 303), the measurement is terminated after the time t has elapsed (see step 304), the concentrations are calculated, and the accuracy of this calculation result (standard deviation) is calculated, which gives results for concentrations and accuracy.

The results for concentration and accuracy are displayed by an LCD or other such display means, and printed out with a printer or the like (see step 306). There are two ways to determine the accuracy of the concentration computation result here: repeating the above-mentioned procedure a number of times (from two to ten), and measuring just once as in the above procedure and then estimating from the X-ray count.

Patent Document 1: Japanese published unexamined patent application H8-43329

DISCLOSURE OF THE INVENTION

However, conventional analysis methods have the following drawbacks.

(1) A concentration calculation result can be obtained only after the elapse of the time (t) set as the measurement time, as performed in step 301, which is inconvenient in terms of operation.

(2) Also, because a concentration calculation result can be obtained only after the set time (t), the measurement time ends up being set longer than necessary in order to measure as accurately as possible the concentration of elements contained in a sample. This drawback will be described by giving an example. When the cadmium concentration was measured in the past using this kind of fluorescent X-ray analysis method, the measurement time t was set as shown in step 301 at the start of the measurement. To measure as accurately as possible, the possibility of the presence of elements other than cadmium was factored in, and the measurement ended up taking an extremely long time of 200 seconds.

Meanwhile, even with a sample that does not contain a large amount of heavy elements such as cadmium, measurement with a conventional analysis method ends up taking 200 seconds. As a result of further investigation, the inventors found that when measuring the cadmium content of a sample based on plastic, there is no need to spend 200 seconds measuring in quantitative analysis of about 20 to 25 ppm, and a measurement time of 10 seconds is sufficient.

Specifically, the problem with conventional analysis methods is that they take as much as 200 seconds even though it can be accurately determined within 10 seconds whether or not a given cadmium concentration is below a specified value.

The present invention was conceived in light of the above problem, which was discovered through experiments conducted by the inventors, and it is an object thereof to provide a fluorescent X-ray analysis method and fluorescent X-ray analysis device with which measurement time can be shortened and the operation made more convenient.

The fluorescent X-ray analysis method according to claim 1 is a fluorescent X-ray analysis method in which the constituent elements of a sample are analyzed from the fluorescent X-rays emitted when the sample is irradiated with X-rays, comprising setting, measuring, deriving, terminating, and outputting. The setting involves setting a sample measurement condition. The measuring involves measuring the fluorescent X-rays. The deriving step involves deriving the measured concentration and measurement accuracy of the constituent elements from the results of the measurement. The terminating involves terminating the measurement of the fluorescent X-rays when the measurement accuracy satisfies the measurement condition. The outputting involves outputting the measured concentration or measurement accuracy.

The phrase "measurement condition" here means a condition upon which measurement is terminated, for example. "Measurement accuracy" is a value expressing the variance or error of a measured concentration.

The fluorescent X-ray analysis method of the present invention comprises a terminating. Accordingly, measurement can be finished in a short time when the measurement accuracy satisfies the desired measurement condition. Specifically, even if the time set as the measurement time has yet to elapse, a measurement result of the desired accuracy can still be obtained. The measurement time can also be shortened.

The fluorescent X-ray analysis method according to claim 2 is the fluorescent X-ray analysis method according to claim 1, wherein the measurement condition is that the measurement accuracy drops below the value derived from a measured concentration.

The "value derived from a measured concentration" is, for example, the product of multiplying a measured concentration by a specific coefficient. In this case, the "measurement condition" is that the measurement accuracy drops below a specific proportion of the measured concentration, for example.

The fluorescent X-ray analysis method pertaining to the present invention allows measurement to be performed at a measurement accuracy corresponding to a measured concentration. Accordingly, the measurement time can be shortened more in the measurement of relatively high concentrations.

The fluorescent X-ray analysis method according to claim 3 is the fluorescent X-ray analysis method according to claim 1, wherein the measurement condition is that the measurement accuracy drops below a predetermined setting value.

The fluorescent X-ray analysis method pertaining to the present invention allows measurement to be performed at a predetermined measurement accuracy regardless of the measured concentration. Accordingly, the measurement time can be shortened more in the measurement of relatively low concentrations.

The fluorescent X-ray analysis method according to claim 4 is the fluorescent X-ray analysis method according to claim 3, wherein the setting value is obtained by dividing the upper limit target value for variance in the measured concentration by an accuracy coefficient that expresses the desired level of accuracy in measurement.

With the fluorescent X-ray analysis method pertaining to the present invention, a setting value obtained by dividing the upper limit target value by an accuracy coefficient is used as the measurement condition. In the measurement of relatively low concentrations, when this measurement condition is satisfied, the measured concentration can be concluded to have dropped below the upper limit target value at a probability determined on the basis of an accuracy coefficient. Accordingly, measurement can be easily performed at a suitable level of accuracy.

The fluorescent X-ray analysis method according to claim 5 is the fluorescent X-ray analysis method according to claim 4, wherein the setting involves inputting at least one of the upper limit target value and the accuracy coefficient.

With the fluorescent X-ray analysis method pertaining to the present invention, it is possible to set the upper limit target value or accuracy coefficient to the desired value.

The fluorescent X-ray analysis method according to claim 6 is the fluorescent X-ray analysis method according to claim 4, wherein the setting involves inputting at least one of the upper limit target value for a plurality of different values and a plurality of the accuracy coefficients corresponding to the various upper limit target values, deriving a plurality of setting value candidates for each of the upper limit target values or accuracy coefficients, and deciding on one of the setting values from the derived plurality of setting value candidates.

With the fluorescent X-ray analysis method pertaining to the present invention, a plurality of pairs of upper limit target value and accuracy coefficient are set. The user can perform measurement using a measurement condition indicated by one of the measurement emit conditions determined from the setting value candidates. For instance, the user can select a more stringent measurement condition according to the accuracy required.

The fluorescent X-ray analysis method according to claim 7 is the fluorescent X-ray analysis method according to claim 1, further comprising evaluating. This evaluating involves evaluating the reliability of measurement from the outputted measured concentration and the measurement accuracy, wherein a comparison is made with threshold values set for the measured concentration and for the measurement accuracy, and the outputted measured concentration and measurement accuracy are ranked on a scale.

The phrase "ranked on a scale" here means, for example, that the measurement values are classified by comparison of measurement values and threshold values, and then evaluated.

With the fluorescent X-ray analysis method pertaining to the present invention, because the measured concentration and the measurement accuracy are ranked on a scale, the user can more easily confirm the measurement results.

The fluorescent X-ray analysis method according to claim 8 is the fluorescent X-ray analysis method according to claim 7, wherein the evaluating involves combining the rankings for measured concentration and measurement accuracy and performing a final evaluation.

With the fluorescent X-ray analysis method pertaining to the present invention, a final evaluation is performed from the scale ranking of the measured concentration and measurement accuracy. Accordingly, the user can more easily confirm the measurement results and can be more easily perform a final determination for the measurement results.

The fluorescent X-ray analysis method according to claim 9 is the fluorescent X-ray analysis method according to claim 7, wherein the setting involves setting the threshold values.

With the fluorescent X-ray analysis method pertaining to the present invention, it is possible to set the threshold value to the desired value.

The fluorescent X-ray analysis device according to claim 10 is a fluorescent X-ray analysis device in which the constituent elements of a sample are analyzed from the fluorescent X-rays emitted when the sample is irradiated with X-rays, comprising an input unit, an irradiation control unit, a detection unit, a computation unit, an output unit, and a control unit. The input unit is for inputting the setting of the sample measurement condition. The irradiation control unit is for controlling X-ray irradiation according to the measurement condition. The detection unit is for detecting the fluorescent X-rays. The computation unit is for computing the measured concentration and measurement accuracy on the basis of signals from the detection unit. The output unit is for outputting the computation result. The control unit is for terminating the measurement of fluorescent X-rays when the measurement accuracy computed by the computation unit satisfies the measurement condition.

The phrase "measurement condition" here means a condition upon which measurement is terminated, for example. "Measurement accuracy" is a value expressing the variance or error of a measured concentration.

The fluorescent X-ray analysis device of the present invention comprises a control unit. Accordingly, measurement can be finished in a short time when the measurement accuracy satisfies the desired measurement condition. Specifically, even if the time set as the measurement time has yet to elapse, a measurement result of the desired accuracy can still be obtained. The measurement time can also be shortened.

In the past, there was the inconvenience of not being able to obtain a concentration calculation result until the time set as the measurement time had elapsed, and the desired measurement accuracy of the concentration calculation result was also not obtained until the set time had elapsed, so to measure the concentration of elements contained in a sample as accurately as possible, the measurement time had to be set longer than necessary, and the measurement time ended up being long, but the present invention prevents this, allowing the measurement time to be shortened and the operation to be made more convenient.

BRIEF DESCRIPTION OF THE DRAWINGS

FIG. 6 is a table for evaluating reliability (Second Embodiment (modification));

FIG. 8 is a table for evaluating reliability (Second Embodiment (modification));

Figure 1:
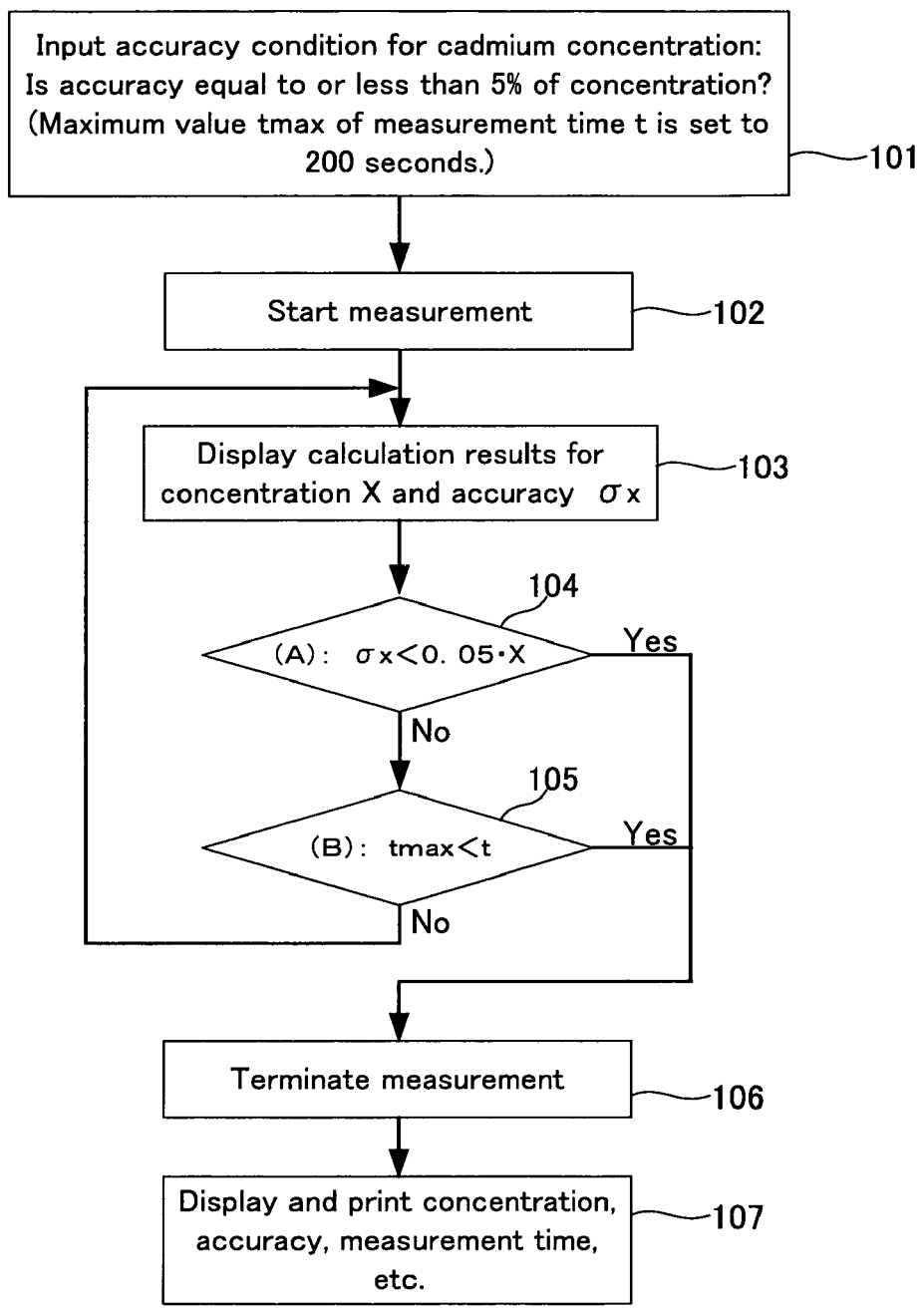
FIG. 1 is a flowchart illustrating First Embodiment of the present invention.

NUMERICAL REFERENCES 201 input component
202 computer
203 controller
204 X-ray tube
205 primary rays
206 sample
207 fluorescent X-rays
208 detector
209 amplifier
210 display component
211 external storage device

DESCRIPTION OF THE PREFERRED EMBODIMENT

Specific embodiments of the present invention will now be described through reference to the drawings.

First Embodiment

Summary

With the present invention, measurement is begun after a sample measurement condition has been set, then the concentrations of elements contained in the sample, and the measurement accuracy thereof (hereinafter referred to as accuracy), are calculated. The measurement is terminated when the calculated value for accuracy reaches a predetermined value, and the concentrations and accuracy at that point are displayed and/or outputted. Therefore, the problems encountered with conventional methods, namely, (1) that operation is inconvenient because the concentration calculation result can be obtained only after the time set as the measurement time has elapsed, and (2) that since the desired measurement accuracy of the concentration calculation result was not obtained until the set time had elapsed, to measure the concentration of elements contained in a sample as accurately as possible, the measurement time had to be set longer than necessary, are solved, allowing the measurement time to be shortened and the operation to be made more convenient.

An embodiment of the present invention will now be described through reference to the drawings.

Constitution

Figure 2:
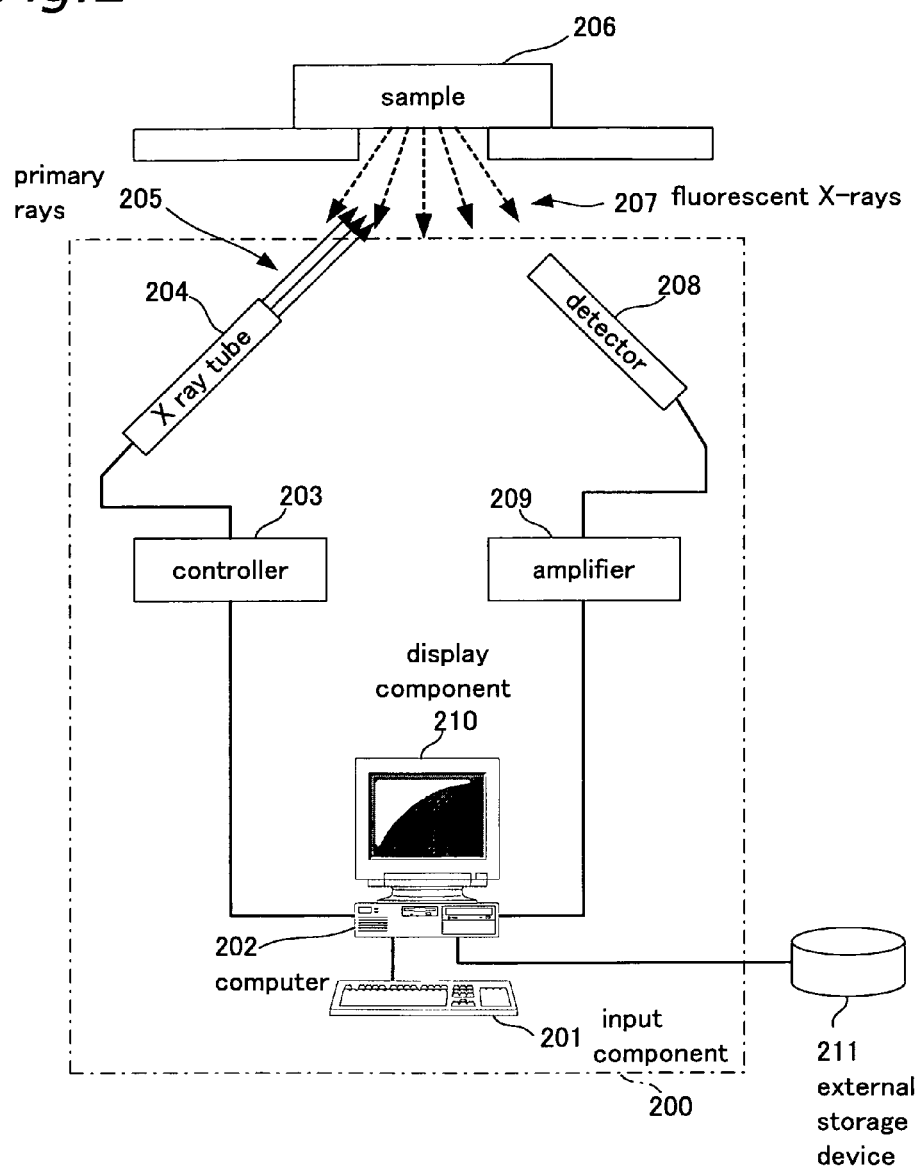
FIG. 2 is a simplified apparatus diagram illustrating First Embodiment of the present invention.

FIG. 1 is a flowchart illustrating First Embodiment of the present invention. FIG. 2 is a simplified apparatus diagram illustrating First Embodiment of the present invention.

In FIG. 2, 201 is an input means consisting of a keyboard or the like for inputting the sample name and the measurement condition (hereinafter referred to as an input component), 202 is a computation means for executing computation processing in which the measurement condition is signal-processed and a spectrum is quantified (hereinafter referred to as a computer), 203 is an irradiation control means for controlling the applied voltage and current of an X-ray tube (hereinafter referred to as a controller), 204 is an X-ray tube for emitting X-rays used for irradiation, 205 is the primary rays that are emitted, 206 is the sample to be measured, 207 is fluorescent X-rays, 208 is a detection means for detecting fluorescent X-rays (hereinafter referred to as a detector), 209 is an amplifier for amplifying the detection signal, 210 is an output means for displaying the computation result and so forth (hereinafter referred to as a display component), and 211 is an external storage device for storing sample information or computation results. The above-mentioned input component 201, computer 202, controller 203, X-ray tube 204, detector 208, amplifier 209, and display component 210 constitute a fluorescent X-ray analysis device 200. The external storage device 211 may also be built-in, rather than just being connected externally to the fluorescent X-ray analysis device 200. The above particulars do not impose any restrictions on the present invention.

Operation

The operation of this device will now be described in detail.

As an example, a method for using the fluorescent X-ray analysis device 200 to measure the cadmium concentration (X wt %; X weight percent) in a plastic resin will be described here through reference to FIGS. 1 and 2. In this embodiment, the description is of a case in which the cadmium concentration is measured, but it should go without saying that the present invention can be used in the analysis of other environmental hazardous substances and other constituent elements.

First, in step 101, the measurement condition is set for the plastic resin sample, after which measurement is begun (see step 102).

Examples of the measurement condition that is inputted here are that the cadmium concentration error must be equal to or less than 5% of the cadmium concentration value, or that the maximum value tmax of the measurement time t does not exceed 200 seconds, for instance. More specifically, the input work may be performed with the input component 201 (keyboard or the like) shown in FIG. 2, or information may be inputted by downloading from the external storage device 211.

Upon receiving the input value, the computer 202 computes the voltage and current applied to the X-ray tube and outputs a command to the controller 203. The controller 203 follows this command and inputs the specified voltage and current to the X-ray tube 204. As a result, the primary rays 205 are emitted by the X-ray tube 204 and irradiate the sample 206. The fluorescent X-rays 207 emitted from the sample 206 are detected by the detector 208, and the detected signal is amplified by the amplifier 209 and returned to the computer 202.

The computer 202 computes the total amount of scattered X-rays (the scattered X-ray count) and the amount of fluorescent X-rays (count value) of cadmium on the basis of the amplified signal. These numerical values and calibration curve constants that have been measured ahead of time are used by the computer 202 to calculate the cadmium concentration X in the plastic resin sample and the measurement accuracy (error) thereof, and the computation results are displayed by the display component 210 (see step 103).

Here, the cadmium concentration X and the measurement accuracy thereof ($\sigma x$) are calculated by using the following equations 1 and 2.

$$X = a \times (F/D) + b \quad (1)$$

In Formula 1, a is a calibration curve constant, D is the count of scattered X-rays, and F is the count for cadmium.

$$\sigma x = a \times (F/D) \times (1/F + 1/D)^{(1/2)} \quad (2)$$

The concentration X and the accuracy $\sigma x$ at the current time given by this computation are displayed as needed on the display screen of the display component 210.

The concentration and the accuracy thereof are then calculated as above whenever needed, and the measurement is terminated when the results for the concentration X and the measurement accuracy $\sigma x$ satisfy the following formula 3.

$$\sigma x < 0.05 \cdot X \quad (3)$$

Specifically, when the measurement accuracy of the computation result from the computer 202 is deemed to be less than a specified value, the flow proceeds to step 106 and the measurement is terminated (see step 106). In Formula 3 above, an inequality sign (<) is used to express the termination condition, but this portion may instead be an inequality sign that includes an equality ($\leq$).

Measurement termination indicates that the computation of the computer 202 has ended and the result has been displayed or outputted, but at the same time the controller 203 may be controlled so that even if the irradiation with the primary rays 205 from the X-ray tube 204 is halted, or if the detection by the detector 208 is ended, amplification by the amplifier 209 will be suspended, for example, or, although not shown in FIG. 2, a mechanical shutter may be provided along the optical path of the primary rays or the fluorescent X-rays so as to cut off the X-rays, or display or output may be fixed even while computation is continuing, or a plurality of these operations may be carried in parallel. Naturally, the method is not limited to those given above.

Meanwhile, in step 104, if the measurement accuracy $\sigma x$ is not less than the specified value, it is determined in step 105 whether or not the measurement time t has exceeded a maximum value tmax of 200 seconds in this measurement. In other words, whether or not the following formula 4 is valid is determined from the measurement condition inputted in step 101.

$$t\max \leq t(\text{measurement time}) \quad (4)$$

In step 105, if it is determined that the measurement time t is over 200 seconds, the flow proceeds to step 106, and the operation of terminating measurement as discussed above is carried out (see step 106).

Finally, in step 107, the results (concentration, accuracy (error), measurement time, etc.) are displayed by the display component 210, and these results are outputted to a printer or external output.

This method may be performed regardless of whether the results are displayed on the display component 210 or are recorded in the external storage device 211. In addition to the measurement results such as concentration, accuracy, and measurement time, it is also preferable to store information about the sample, such as its size, shape, or material, ahead of time in the external storage device 211, although this is not a requirement.

The sample 206 has to be taken out upon termination of measurement, but since worker safety may be in danger while the primary rays 205 are being released, it is preferable to quickly halt the release of the primary rays 205 upon termination of the measurement. More specifically, in step 106 when measurement is terminated and it is confirmed that the results have been displayed on the display component 210, it is preferable to add a function whereby a halt signal is sent from the computer 202 to the controller 203, and the controller 203 stops the operation of the X-ray tube 204.

Ways to ensure worker safety include a method in which the controller 203 is controlled so as to halt irradiation with the primary rays 205 emitted from the X-ray tube 204, a method in which the detection by the detector 208 is halted, and a method in which a shutter is provided along the optical path of the primary rays, although other methods are also possible.

With this embodiment, the person taking the measurement inputs or downloads the required values ahead of time, so that a determination can be automatically made from indexes A (see step 104 in FIG. 1) and B (see step 105 in FIG. 1) for determining calculated values, and the measurement can be terminated. Accordingly, the person does not necessarily have to wait for the output of the measurement results until the set time has elapsed, allowing the measurement time to be shortened and the operation to be made more convenient.

To obtain a result with sufficient reliability in the measurement of the cadmium concentration of a plastic resin in this embodiment, a required value of 5% was inputted on the basis of a preliminary experiment result indicating that the accuracy needed to be 5% or less corresponding to $2\sigma$ of the measurement value, but the present invention is not limited to this, and a smaller value may be inputted if greater accuracy is needed, or a larger value may be used.

Also, if the element to be measured is contained in an extremely small amount, the calculation result may not fit in a percentage display of the content. In such a case, it may be better not to define the required accuracy by a decimal content, and instead to define it by the variance in the absolute count, because this may yield good results at higher speed, but the present invention is not limited to this, of course.

Second Embodiment

Summary

Second Embodiment provides different processing in the computer 202 (see FIG. 2). More specifically, a measurement condition that is different from that of First Embodiment is set in the computer 202, and measurement is performed. A detailed description is given below, but a description of the structure of the fluorescent X-ray analysis device 200 is omitted because it is the same as in First Embodiment.

Operation

Second Embodiment of the present invention will be described through reference to the flowchart shown in FIG. 3.

First, the measurement condition for a plastic resin sample is set in step 121, after which measurement is begun (see step 122).

In the setting of the measurement condition, the upper limit target value for variance in the measured concentration, and an accuracy coefficient indicating the desired level of accuracy in the measurement are inputted.

The upper limit target value for variance is a value determined as desired by the user, but when, for example, the user determines his own management criterion (this is a value that limits the concentration in which an environmental hazardous substances is contained in a part, such as a value that is lower than the concentration limit prescribed by law), this management criterion is inputted.

The accuracy coefficient is a value determined as desired by the user, and a value indicating the probability at which the measurement accuracy value will be under the upper limit target value (that is, a value indicating the level of measurement accuracy) is inputted.

Further, the maximum value tmax for measurement time is inputted just as in First Embodiment. tmax is set to 200 seconds just as in First Embodiment.

These inputs are performed using the input component 201 (a keyboard or the like) shown in FIG. 2, or by downloading from the external storage device 211.

The inputted values are set in the computer 202.

In steps 122 and 123, just as in steps 102 and 103 of First Embodiment, the fluorescent X-rays 207 are detected and the measured concentration X and measurement accuracy σx are calculated on the basis of Formulas 1 and 2. This will not be described in detail as it is the same as in First Embodiment.

In step 124, measurement is terminated when the measurement accuracy σx calculated in step 123 satisfies the following formula (3').

$$\sigma x < (\sigma 1/k1) \quad (3')$$

Here, σ1 is the upper limit target value set in step 121, and k1 is the value of the accuracy coefficient set in step 121.

Specifically, when it is determined that the measurement accuracy of the calculation result in the computer 202 is less than the set value (σ1/k1), the flow proceeds to step 126 and the measurement is terminated (see step 126). In this Formula 3', an inequality sign (<) is used to indicate the measurement condition, but this portion may instead be an inequality sign that includes an equality (≦).

The processing involved in terminating the measurement in step 126 here will not be described as it is the same as in First Embodiment.

Meanwhile, in step 124, if the measurement accuracy σx is not less than the set value (σ1/k1), the flow proceeds to step 125. In step 125, it is determined whether or not the measurement time t is over the maximum value tmax set in step 121 (set to 200 seconds in this embodiment). The processing involved in step 125 will not be described as it is the same as in First Embodiment.

In step 125, if it is determined that the measurement time t is over the maximum value tmax (200 seconds), the flow proceeds to step 126 and processing for measurement termination is executed (see step 126).

Finally, in step 127, the results (concentration, accuracy (error), measurement time, etc.) are displayed by the display component 210, and these results are outputted to a printer or external output.

Effect

Thus, with this embodiment, the measurement time can be shortened and operation made more convenient without necessarily having to wait for the output of measurement results until the set time has elapsed.

Also, with a sample that contains almost no environmental hazardous substances, and the measurement result for the measured concentration X is substantially outputted as 0 ppm, the upper limit target value set in step 121 is used as a user management criterion, so that the actual concentration will be under the management criterion at a probability based on a value determined by an accuracy coefficient. Specifically, it can be confirmed that a value of 0 ppm given as the measurement result for the measured concentration X is a value that can be trusted, and it can be confirmed that the management criterion of the user is satisfied. Ordinarily, the user's management criterion is set to be well under (such as less than 25 ppm in the case of cadmium) the value prescribed by law (with RoHS, for example, less than 100 ppm cadmium). Accordingly, when the present invention is employed, it can more easily be determined whether or not a sample to be measured satisfies a legal limit, and furthermore, it can be determined whether or not a user's management criterion is satisfied.

Figure 4:
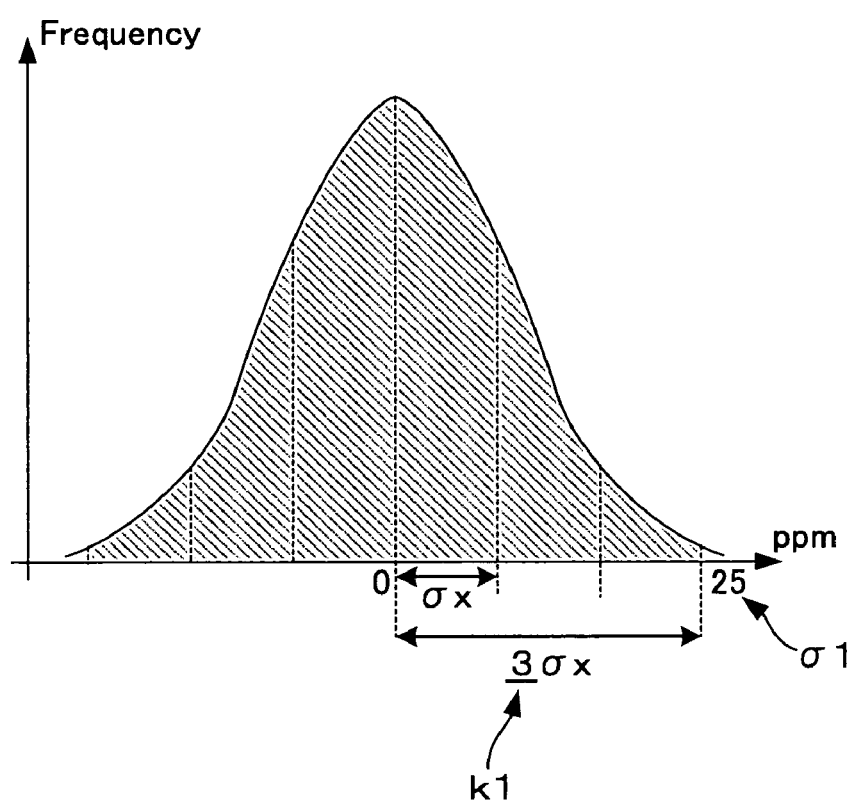
FIG. 4 is a graph of the distribution of the measured concentration X (ppm) (Second Embodiment)

The relation between the measurement accuracy σx, the upper limit target value σ1, and the accuracy coefficient k1 will now be discussed through reference to FIG. 4. FIG. 4 is a graph of the distribution of measured concentration X (ppm). The measurement accuracy σx is a value indicating the deviation from the average distribution. The accuracy coefficient k1 is a coefficient that determines the reliable range, and in FIG. 4 this reliable range is a range that is three times the measurement accuracy σx (that is, k1=3). The significance of the processing in step 124 using Formula 3' is that the measurement is terminated when the upper limit target value σ1 (25 ppm in FIG. 4) falls within a range of three times the measurement accuracy σx.

In FIG. 4, the value of the accuracy coefficient k1 is given as 3, but this value can be changed as needed according to the accuracy desired by the user. For instance, if the accuracy does not need to be that high, the value may be set lower so that the processing is terminated in less time. If greater accuracy is required, then the value may be set higher. When measurement accuracy and processing time are comparatively taken into account, it is preferable for the value of the accuracy coefficient k1 to be about 2 to 6.

Modifications (1)

(1-1)

The invention of Second Embodiment may further comprise a step of evaluating the reliability of the values of the measurement accuracy σx and the measured concentration X upon termination of measurement. More specifically, the measurement accuracy σx and the measured concentration X upon termination of measurement are each compared with threshold values. The reliability of a measurement result is evaluated on the basis of this comparison. This will be described through reference to the flowchart in FIG. 5.

When the measurement is terminated in step 126 (see FIG. 3), the computer 202 (see FIG. 2) evaluates the measurement result (step 130). More specifically, it is determined whether or not the measured concentration X upon termination of measurement is under a threshold value Xt related to a predetermined concentration (whether or not condition X<Xt), and whether or not the measurement accuracy σx upon termination of measurement is under a threshold value σt related to a predetermined accuracy (whether or not condition σx<σt), and the result of each determination is displayed with a symbol or the like. In this display of determination results, for instance, a "○" is displayed if the condition is met, and a "×" if the condition is not met. The display of determination results is not limited to this, however, and any kind of display may be used, but it is preferably a display that will be easy for the user to recognize.

Figure 3:
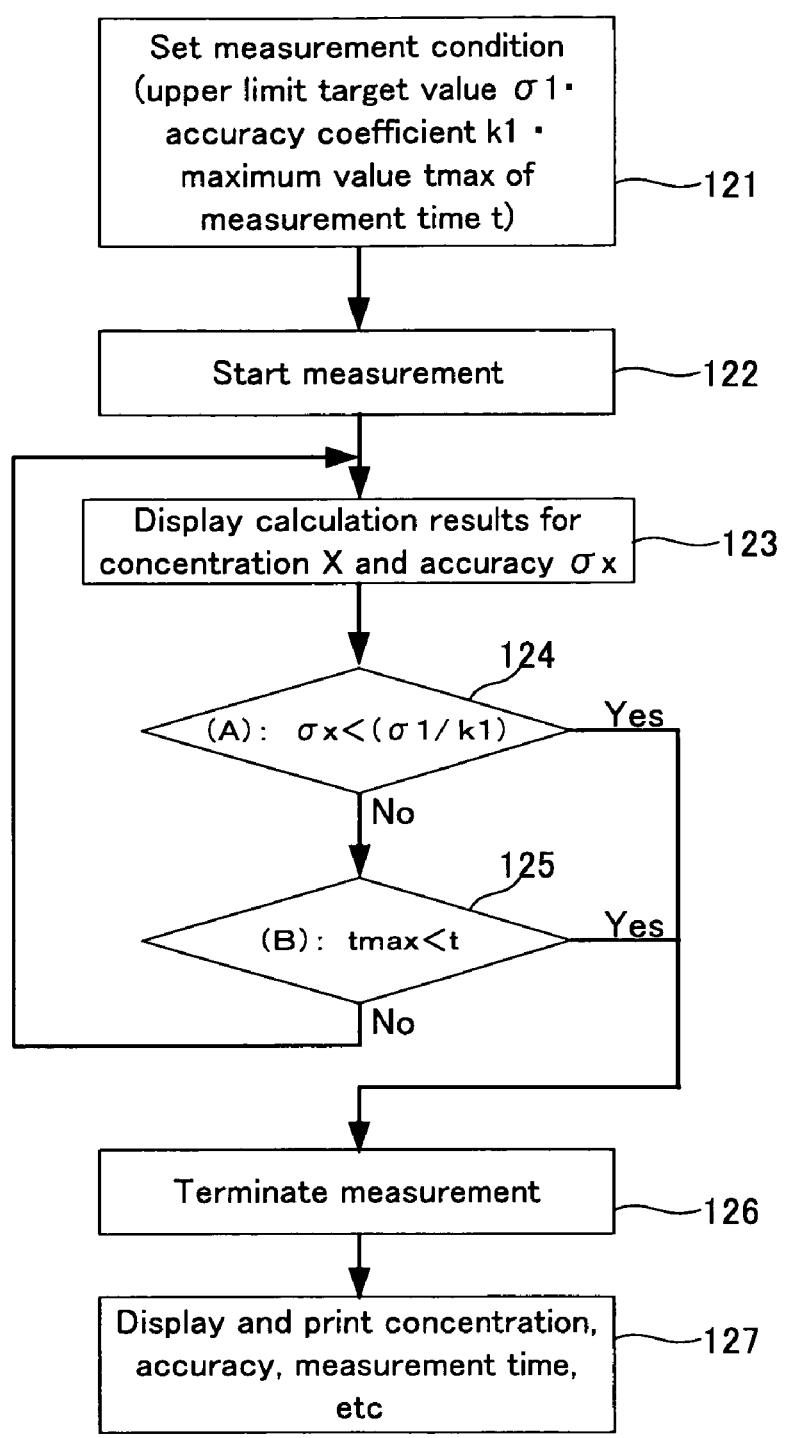
FIG. 3 is a flowchart illustrating Second Embodiment of the present invention.

Here, the threshold value Xt and the threshold value at are set ahead of time in step 121 (see FIG. 3). The threshold value at may be the same as the upper limit target value σ1 set in step 121. In this case, if the user inputs the upper limit target value σ1, this value will be automatically set to the threshold value σt. The threshold value Xt may also be the same as the upper limit target value σ1 set in step 121.

In step 131, the result of determining the measured concentration X is combined with the result of determining the measurement accuracy σx, and the reliability of the measurement as a whole is evaluated. A table for evaluating reliability is stored ahead of time in the external storage device 211 or a memory provided to the computer 202.

FIG. 6 shows this table Tb1. In table Tb1, the reliability evaluation result is correlated with the combination of the determination results for step 130. The computer 202 uses the determination results of step 130 and refers to the table Tb1 to output a reliability evaluation result. Let us describe an example. When the determination result for measured concentration X is "○" and the determination result for measurement accuracy σx is "×," for example, an assessment result of "?" is outputted, and an evaluation result of "high analysis accuracy required" is outputted.

The table Th1 contains as the assessment result whichever of the measured concentration X and the measurement accuracy σx has the worse determination results. If the determination result for the measurement accuracy σx is "×," then "?" is stored as the assessment result. Consequently, the reliability of the measurement itself is deemed low if the determination result for the measurement accuracy σx is "×," and otherwise, the reliability of the measurement itself is high when the determination result for the measured concentration X is "×," but it is deemed that there is a problem with the sample.

Finally, in step 132, the results (measured concentration, measurement accuracy (error), measurement time, reliability evaluation result) are displayed by the display component 210, and these results are outputted to a printer or external output.

With the present invention, since the reliability of the measurement results is evaluated, the user can easily ascertain how good the measurement results are, and then decide what action to take.

Figure 5:
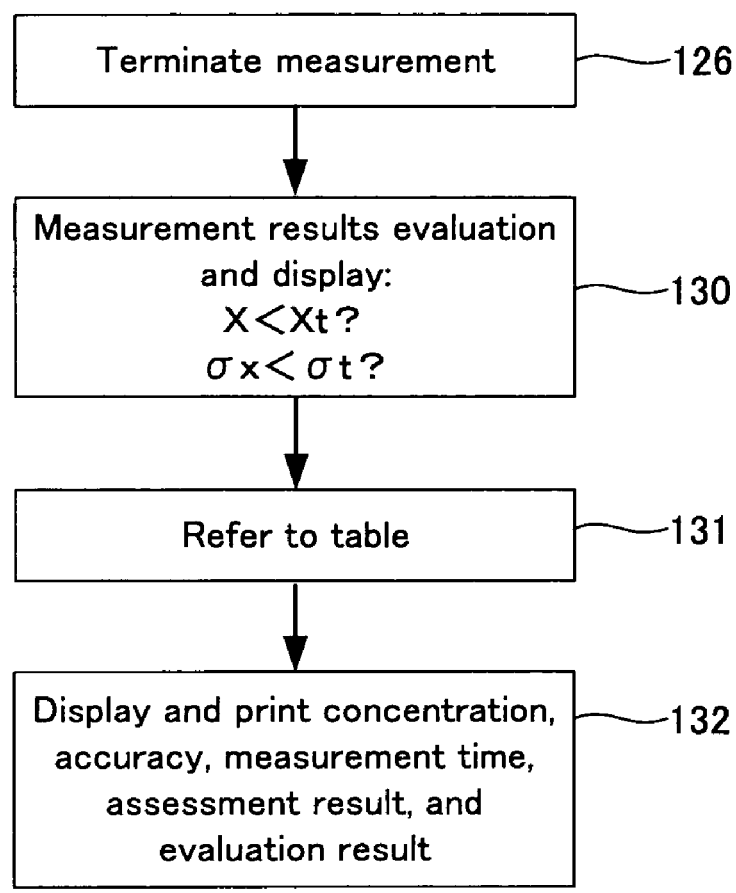
FIG. 5 is a flowchart illustrating Second Embodiment (modification) of the present invention.

The processing in FIG. 5 can also be applied with common-sense changes in First Embodiment. The table Tb1 shown in FIG. 6 is just an example, and the present invention is not limited to or by this example. The user can change the contents of the table Tb1 or the threshold values as necessary.

(1-2)

Figure 7:
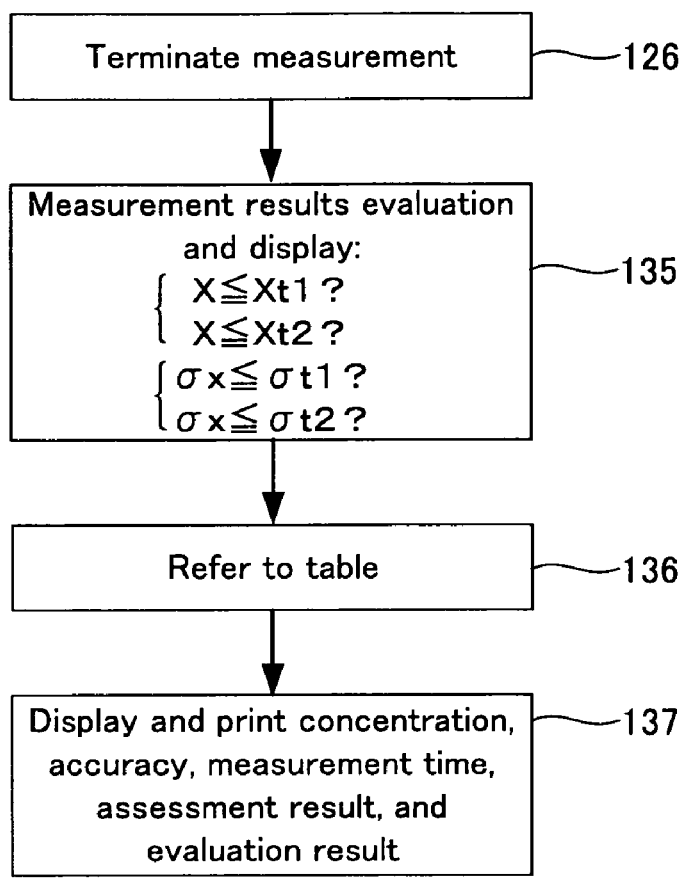
FIG. 7 is a flowchart illustrating Second Embodiment (modification) of the present invention.

In section 1-1 above, the measured concentration X and the measurement accuracy σx may also each be compared with two threshold values. This will be described through reference to the flowchart in FIG. 7.

When the measurement is terminated in step 126 (see FIG. 3), the computer 202 (see FIG. 2) evaluates the measurement result (step 135). More specifically, first, it is determined whether or not the measured concentration X upon termination of measurement is under two threshold values Xt1 and Xt2 (where Xt1<Xt2) related to a predetermined concentration (that is, two conditions are determined, namely, whether or not the condition X≦Xt1 is satisfied, and whether or not the condition X≦Xt2 is satisfied). Also, it is determined whether or not the measurement accuracy σx upon termination of measurement is under two threshold values σt1 and σt2 (where σt1<σt2) related to a predetermined accuracy (that is, two conditions are determined, namely, whether or not the condition σx≦σt1 is satisfied, and whether or not the condition σx≦σt2 is satisfied). The results of these determinations are combined to determine the magnitude relationship of the measured concentration X to the threshold value Xt1 and the threshold value Xt2, and the magnitude relationship of the measurement accuracy σx to the threshold value σt1 and the threshold value σt2. The magnitude relationship of the measured concentration X or the measurement accuracy σx to their respective threshold values does not have to be determined as above, and can be determined by any of various kinds of processing.

The determination results are displayed with a symbol or the like. In this display of determination results, a "○" is displayed if the measured concentration X satisfies X≦Xt1, a "Δ" if it satisfies Xt1<X≦Xt2, and a "×" if it satisfies Xt2<X. Just as in the case of the measurement accuracy σx, a "○" is displayed if the measurement accuracy σx satisfies σx≦σt1, a "Δ" if it satisfies σt1<σx≦σt2, and a "×" if it satisfies σt2<σx. The display of determination results is not limited to this, however, and any kind of display may be used, but it is preferably a display that will be easy for the user to recognize.

Here, the threshold values Xt1 and Xt2 and the threshold values σt1 and σt2 are set ahead of time in step 121 (see FIG. 3). The threshold value σt1 may be the same as the upper limit target value σ1 set in step 121. Further, the threshold value σt2 may be set to a value that is greater than the upper limit target value σ1, and a value (such as 70 ppm) that does not exceed the value prescribed by law (100 ppm in the case of cadmium, for example), and so on. The threshold values Xt1 and Xt2 may be the same as the threshold values σt1 and σt2 set in step 121. In this case, if the user inputs the threshold values σt1 and σt2, these values will be automatically set to the threshold values Xt1 and Xt2.

In step 136, the determination results for the measured concentration X are combined with the determination results for the measurement accuracy σx, and the reliability of the measurement as a whole is evaluated. A table for evaluating reliability is stored ahead of time in the external storage device 211 or a memory provided to the computer 202.

FIG. 8 shows this table Tb2. In table Tb2, the reliability evaluation result is correlated with the combination of the determination results from step 135. The computer 202 uses the determination results of step 135 and refers to the table Tb2 to output a reliability evaluation result. Let us describe an example. When the determination result for measured concentration X is "○" and the determination result for measurement accuracy σx is "x," for example, an assessment result of "?" is outputted, and an evaluation result of "high analysis accuracy required" is outputted.

In the table Tb2, the reliability of the measurement itself is low when the determination result for the measurement accuracy σx is "x," so an evaluation result indicating that analysis be performed by a method of even higher accuracy is outputted. The table Tb2 is also such that the reliability of the measurement itself is inadequate when the determination result for the measurement accuracy σx is "Δ," so an evaluation result indicating that the test be performed again, such as changing the sample and re-measuring, or conducting the measurement for a longer time than what was set, is outputted. In other cases, the table Tb2 contains as the assessment result whichever of the measured concentration X and the measurement accuracy σx has the worse determination results. For instance, if the determination result for the measured concentration X is "x" or "Δ," the reliability of the measurement itself is high, but there is a problem with the sample, so an evaluation result corresponding to either case is outputted.

Finally, in step 137, the results (measured concentration, measurement accuracy (error), measurement time, reliability evaluation result) are displayed by the display component 210, and these results are outputted to a printer or external output.

With the present invention, since the reliability of the measurement results is evaluated, the user can easily ascertain how good the measurement results are, and then decide what action to take.

The table Tb2 shown in FIG. 8 is just an example, and the present invention is not limited to or by this example. The user can change the contents of the table Tb2 or the threshold values as necessary.

(2)

In Second Embodiment, it was described that the upper limit target value σ1 and the accuracy coefficient k1 were both inputted in step 121 (see FIG. 3). Here, in step 121, just one of these values may be inputted. In this case, the one that was not inputted is set to a default value. The default value is stored ahead of time in a memory or the like by the computer 202, or is stored in the external storage device 211. Also, the same applies to the threshold values described in Modification (1), and a default value may be used for the value not inputted.

(3)

In Second Embodiment, the value for the measurement accuracy σx was based on Formula 2. Here, the value for measurement accuracy may be found from the following formula (5).

$$\sigma x = (BG/T)^{(1/2)} \quad (5)$$

Here, BG is the blank sample gross strength (cps) per unit of time, and T is the effective measurement time (live time) (seconds).

Third Embodiment

Summary

A user usually determines his own management criterion for the concentration of environmental hazardous substances contained in the parts of a product, and there may be more than one criterion. For instance, examples of management criteria include a management criterion that "is under a management criterion value determined on the basis of the smallest detectable amount of the element to be measured," and a management criterion that "is not over a management criterion value determined on the basis of the smallest amount that can be detected at sufficient reliability with a given analysis method).

The present invention proposes an analysis method that shortens measurement time and makes operation more convenient, just as in Embodiments 1 and 2, and that allows an assessment result to be obtained which satisfies, with sufficient reliability, the above-mentioned plurality of management criteria and legal limits.

More specifically, Third Embodiment provides still different processing in the computer 202 (see FIG. 2). The processing of the present invention is different from that in Second Embodiment in step 121 of Second Embodiment (see FIG. 3), and instead a plurality of upper limit target values ($\sigma 1, \sigma 2, \ldots$) and a plurality of accuracy coefficients ($k1, k2, \ldots$) are inputted. This will be described in detail below, but the structure of the fluorescent X-ray analysis device 200 (see FIG. 2) will not be described again as it is the same as that in First Embodiment.

Operation

The invention in Third Embodiment will be described through reference to the flowchart shown in FIG. 9.

First, in step 141a, measurement is begun after a measurement condition for a plastic resin sample has been set (see step 142).

In step 141a, in the setting of the measurement condition, the upper limit target value for variance in the measured concentration, and an accuracy coefficient indicating the desired level of accuracy in this upper limit target value, are inputted in two pairs. Specifically, accuracy coefficients k1 and k2 are inputted for two upper limit target values σ1 and σ2 (where $\sigma 1 \leq \sigma 2$). In this embodiment, the description is of a case in which two of each value are inputted, but the present invention can also be expanded to a case in which more values are inputted.

Furthermore, in step 141a, the maximum value tmax of the measurement time is inputted just as in First Embodiment. We will assume that tmax is set to 200 seconds just as in First Embodiment.

These inputs are performed using the input component 201 (a keyboard or the like) shown in FIG. 2, or by downloading from the external storage device 211, just as in First Embodiment.

The inputted values are stored in a memory provided to the computer 202.

The computer 202 determines whether or not an acquired value satisfies the following formula (6) (step 141b).

$$(\sigma 1/k1) < (\sigma 2/k2) \quad (6)$$

If the determination in step 141b is positive (that is, if the inequality (σ1/k1)<(σ2/k2) is true), then (σ1/k1) is stored as a setting value for the measurement condition at a specific address in the memory of the computer 202 (step 141c).

If the assessment in step 141b is negative (that is, if the inequality (σ1/k1)<(σ2/k2) is not true), then (σ2/k2) is stored as a setting value for the measurement condition at a specific address in the memory of the computer 202 (step 141d).

Specifically, in step 141, which pertains to the setting of the measurement condition, whichever of (σ1/k1) and (σ2/k2) is less is set as the setting value for the measurement condition. This method for determining the setting value is just an example, and the user can determine the setting value as desired, according to the desired measurement accuracy. For instance, the setting value for the measurement condition may be whichever of ($\sigma 1/k1$) and ($\sigma 2/k2$) is greater, or the average of these may be used as the setting value.

In steps 142 and 143, just as in steps 102 and 103 of First Embodiment, the fluorescent X-rays 207 are detected and the measured concentration X and measurement accuracy $\sigma x$ are calculated on the basis of Formulas 1 and 2. This will not be described in detail as it is the same as in First Embodiment.

In step 144, it is assessed whether or not the value of measurement accuracy $\sigma x$ satisfies a specific condition. A characteristic of this embodiment is that different assessment conditions are used according to the value of the measured concentration X.

First, it is assessed whether or not the measured concentration X satisfies Formula 7 (step 144a).

$$(X/9) < \alpha \quad (7)$$

If the assessment in step 144a is positive, it is assessed whether or not the measurement accuracy $\sigma x$ satisfies Formula (8) (step 144b).

$$\sigma x < \alpha \quad (8)$$

$\alpha$ here is the setting value set in step 141c or step 141d, and is read out from a specific address in the memory of the computer 202.

If the assessment in step 144b is positive, that is, if the measurement accuracy $\sigma x$ of the calculation result in the computer 202 is determined to be less than the setting value $\alpha$, the flow proceeds to step 146 and measurement is terminated (see step 146).

The processing involved in terminating the measurement in step 146 here will not be described as it is the same as in First Embodiment.

Meanwhile, if the assessment is negative in step 144b, that is, if the measurement accuracy $\sigma x$ is not less than the setting value $\alpha$, the flow proceeds to step 145. The processing in step 145 will be discussed below.

Next, if the assessment is negative in step 144a, it is determined whether or not the measurement accuracy $\sigma x$ satisfies Formula 9, which is a function of the measured concentration X (step 144c).

$$\sigma x < (X/9) \quad (9)$$

If the assessment in step 144c is positive, the flow proceeds to step 146 and measurement is terminated (see step 146).

Meanwhile, if the assessment is negative in step 144c, the flow proceeds to step 145.

Figure 10:
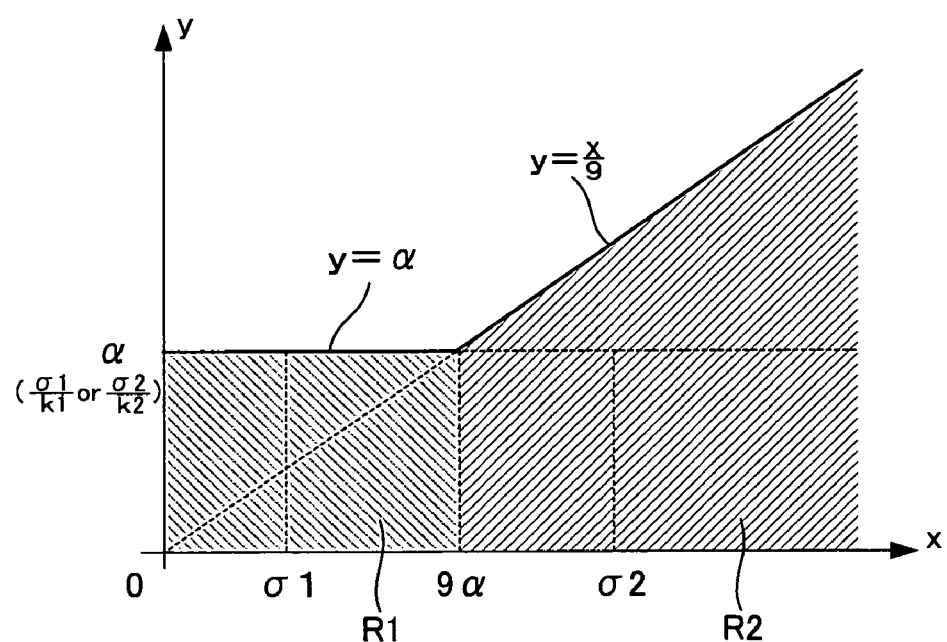
FIG. 10 is a graph complementarily illustrating the processing in step 144 (Third Embodiment)
Figure 11:
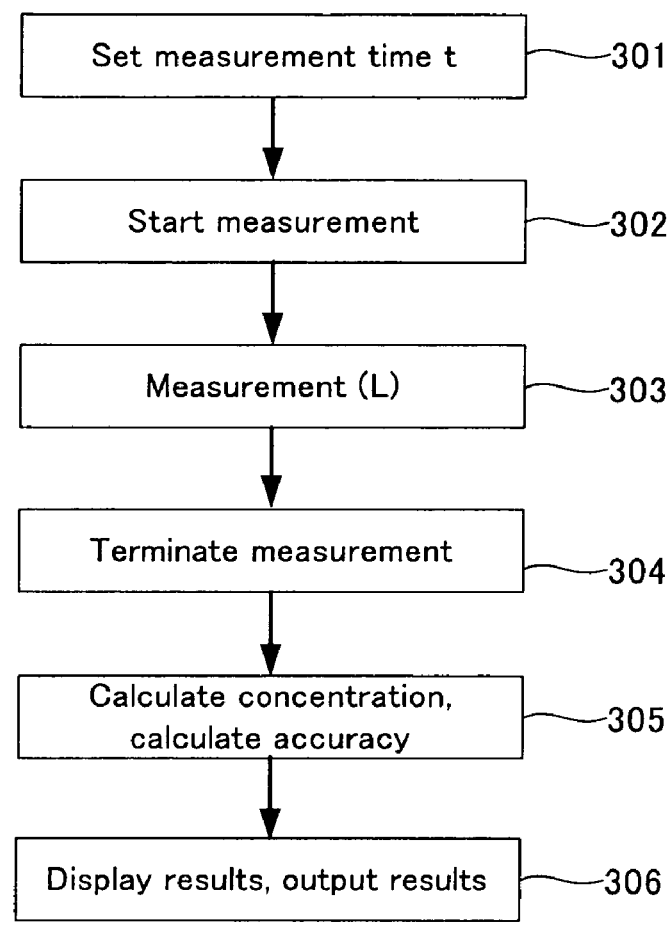
FIG. 11 is a flowchart illustrating a conventional example (prior art).

At this point, before describing step 145, let us refer to FIG. 10 to describe complementarily the significance of the processing in step 144.

FIG. 10 is a graph in which the horizontal axis (x axis) is the measured concentration X, and the vertical axis (y axis) is the measurement accuracy $\sigma x$. The region in which the assessment is satisfied in step 144 is indicated with diagonal lines.

In particular, in the first quadrant, the region R1 in which $y < \alpha$ and $x < (9\alpha)$ are satisfied indicates the region in which the assessment of step 144b is satisfied. Also, in the first quadrant, the region R2 in which $y < (x/9)$ and $(9\alpha) \leq x$ are satisfied indicates the region in which the assessment of step 144c is satisfied.

The assessment of measurement accuracy $\sigma x$ is performed under these conditions for the following reason.

First, when the measured concentration X is relatively low ($X < (9\alpha)$), an assessment is performed of the measurement accuracy $\sigma x$ and the setting value $\alpha$ which is the smaller of ($\sigma 1/k1$) and ($\sigma 2/k2$), and measurement is performed until whichever of the measurement conditions set in step 141a is more stringent is satisfied.

Meanwhile, when the measured concentration X is relatively high ($(9\alpha) \leq X$), there is little probability that the measurement accuracy $\sigma x$ will go under the setting value a within the measurement time, and the operation usually times out (that is, the measurement is terminated by the condition related to time, out of the measurement conditions). Accordingly, for a sample such as this, the overall measurement efficiency is improved by a method such as finishing up measurement earlier by using a relatively moderate termination condition, and performing analysis by another method.

The processing shown in step 144 is performed for the above reason. Measurement under this condition is preferable, but is not absolutely necessary, and instead all of the measured concentrations X may just be compared with the same setting value $\alpha$. Also, the slope of the line $y=(x/9)$ that defines the region R2 is not limited to this, but may be defined as the inverse of the accuracy coefficient k1 or k2.

In step 145, it is determined whether or not the measurement time t exceeds the maximum value tmax set in step 141a (set to 200 seconds in this embodiment). The processing involved in step 145 here will not be described as it is the same as in First Embodiment.

If it is determined in step 145 that the measurement time t has exceeded the maximum value tmax (200 seconds), the flow proceeds to step 146 and measurement termination processing is executed (see step 146).

Finally, in step 147, the results (concentration, accuracy (error), measurement time, etc.) are displayed by the display component 210, and these results are outputted to a printer or external output.

Effect

Thus, in this embodiment, the set time can be shortened and operation made more convenient without necessarily having to wait for the output of measurement results until the measurement time has elapsed.

Also, measurement results can be obtained which satisfy, with sufficient reliability, a plurality of management criteria and legal limits. This will be described in a little more detail below.

Let us assume, for example, that a user has specified a plurality of management criteria, namely, "that the cadmium content be under 25 ppm" and "that the cadmium content not be over 70 ppm," with respect to a legal limit (cadmium content of less than 100 ppm). Let us further assume that the latter is measured at a certainty of about three times that of the former. More specifically, for example, in step 141a the settings are ($\sigma 1$, $k1$)=(25 ppm, 3), ($\sigma 2$, $k2$)=(70 ppm, 9), and so forth.

When the sample to be measured contains substantially no environmental hazardous substances, and the measurement result for the measured concentration X is usually outputted as 0 ppm, the upper limit target value set in step 141a is used as the user's management criterion, so that the actual concentration will be under the management criterion at a probability based on a value determined by an accuracy coefficient. Furthermore, in actual processing, a measurement result that sufficiently satisfies the user's management criterion can be obtained by assessing with the more stringent of the measurement conditions set from the two pairs of values. The user's management criterion is set to a value that is under the value prescribed by law (with RoHS, for example, less than 100 ppm cadmium). Accordingly, when the present invention is employed, it can more easily be determined whether or not a plurality of management criteria specified by the user are satisfied, and whether or not a legal criterion is satisfied.

The values of the accuracy coefficients here were k1=3 and k2=9, but the present invention is not limited to this case, and these values can be changed as desired according to the accuracy desired by the user. For instance, if not that much accuracy is needed, the values can be set lower to end the processing in a shorter time. If higher accuracy is needed, the values can be set higher.

Modifications (1)

The invention of Third Embodiment may further comprise a step of evaluating the reliability of the values of the measurement accuracy σx and the measured concentration X upon termination of measurement, just as in Modification (1) of Second Embodiment. More specifically, the measurement accuracy σx and the measured concentration X upon termination of measurement are each compared with threshold values. The reliability of a measurement result is evaluated on the basis of this comparison.

For instance, just as in section (1-2) in Modification (1) of Second Embodiment, the measured concentration X and the measurement accuracy σx may be compared with two threshold values. The processing here will not be described in detail as it is the same as that in section (1-2) in Modification (1) of Second Embodiment.

Figure 9:
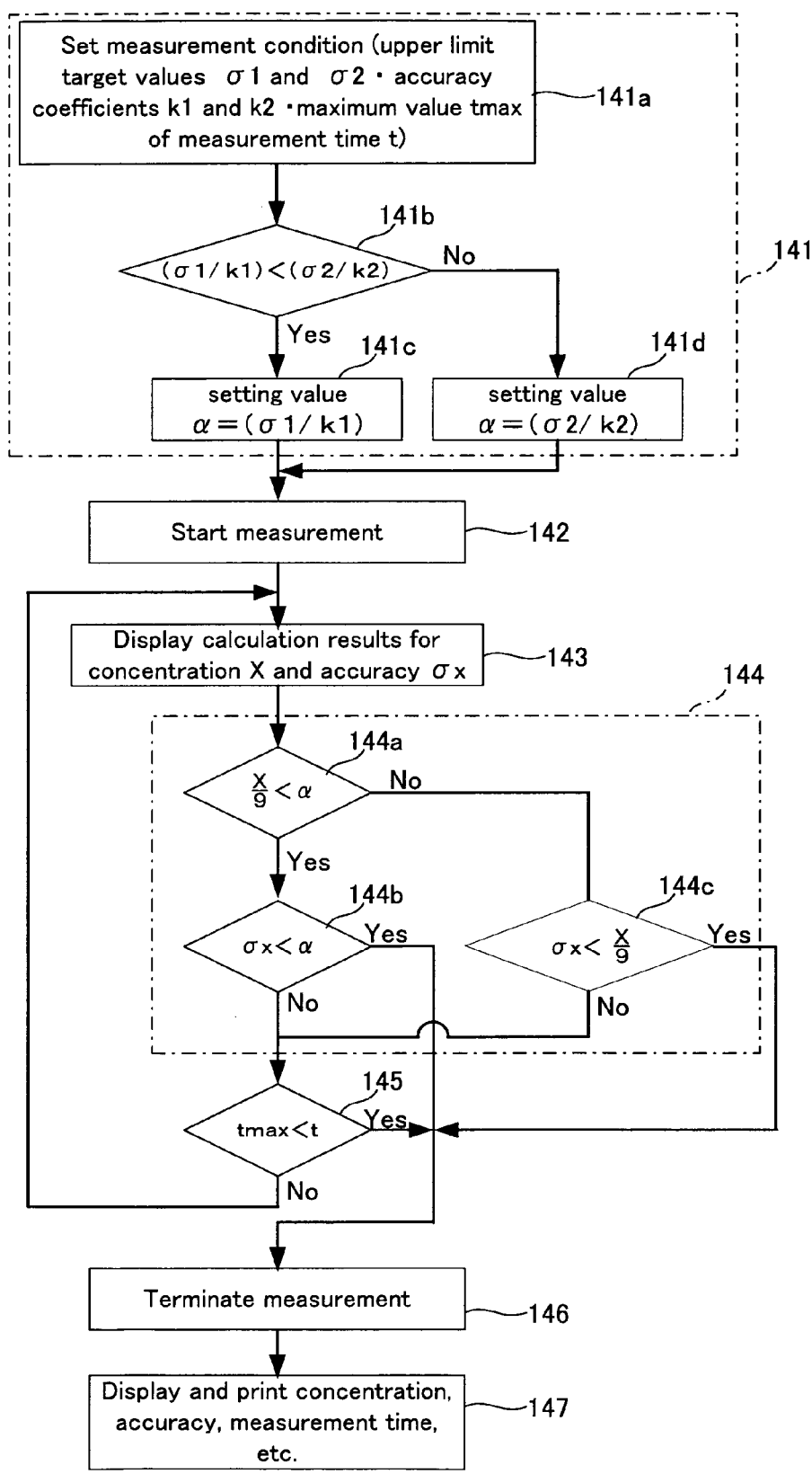
FIG. 9 is a flowchart illustrating Third Embodiment of the present invention.

In this case, the threshold values Xt1 and Xt2 and the threshold values σt1 and σt2 are set ahead of time in step 141a (see FIG. 9). The threshold values σt1 and σt2 may be the same as the upper limit target values σ1 and σ2 set in step 141a. In this case, if the user inputs the upper limit target values σ1 and σ2, these values will be automatically set to the threshold values σt1 and σt2. The threshold values Xt1 and Xt2 may be the same as the upper limit target values σ1 and σ2 set in step 141a.

With the present invention, since the reliability of the measurement results is evaluated, the user can easily ascertain how good the measurement results are, and then decide what action to take.

(2)

In the above embodiment, it was explained that the value of α may be set to whichever of (σ1/k1) and (σ2/k2) is less or greater, an average value, or the like.

Also, the value of α may be determined according to the value of the measured concentration X. For instance, within the range of 0≦X≦σ1, (σ1/k1) may be used as the setting value, and within the range of σ1<X, (σ2/k2) may be used as the setting value.

In this case, in the processing shown in FIG. 9, the processing of steps 141b to 141d is not performed. Also, in step 144a, the calculation of Formula 7 is performed using a setting value α corresponding to the value of X. Further, in step 144b, the calculation of Formula 8 is performed using a setting value α corresponding to the value of X.

INDUSTRIAL APPLICABILITY

The fluorescent X-ray analysis method and fluorescent X-ray analysis device pertaining to the present invention are useful in fields in which measurement time needs to be shortened and operation needs to be made more convenient.

The invention claimed is:

1. A fluorescent X-ray analysis method in which the constituent elements of a sample are analyzed from the fluorescent X-rays emitted when the sample is irradiated with X-rays, comprising:
    setting a sample measurement condition;
    measuring the fluorescent X-rays;
    deriving the measured concentration and measurement accuracy of the constituent elements from the results of the measurement;
    terminating the measurement of the fluorescent X-rays when the measurement accuracy satisfies the measurement condition; and
    outputting the measured concentration or measurement accuracy, wherein
    the measurement condition is that the measurement accuracy drops below a predetermined setting value,
    the setting value is obtained by dividing the measured concentration by a predetermined value.

2. A fluorescent X-ray analysis method in which the constituent elements of a sample are analyzed from the fluorescent X-rays emitted when the sample is irradiated with X-rays comprising:
    setting a sample measurement condition;
    measuring the fluorescent X-rays;
    deriving the measured concentration and measurement accuracy of the constituent elements from the results of the measurement;
    terminating the measurement of the fluorescent X-rays when the measurement accuracy satisfies the measurement condition; and
    outputting the measured concentration or measurement accuracy, wherein
    the measurement condition is that the measurement accuracy drops below a calculation value obtained by dividing the measured concentration by a predetermined value when the calculation value is larger than a predetermined setting value, or that the measurement accuracy drops below the calculation value when the calculation value is smaller than the setting value.

3. The fluorescent X-ray analysis method according to claim 2, wherein the setting value is obtained by dividing the upper limit target value for variance in the measured concentration by an accuracy coefficient that expresses the desired level of accuracy in measurement.

4. The fluorescent X-ray analysis method according to claim 3, wherein the setting involves inputting at least one of the upper limit target value and the accuracy coefficient.

5. The fluorescent X-ray analysis method according to claim 3, wherein the setting involves inputting at least one of the upper limit target value for a plurality of different values and a plurality of the accuracy coefficients corresponding to the various upper limit target values, deriving a plurality of setting value candidates for each of the upper limit target values or accuracy coefficients, and deciding on one of the setting values from the derived plurality of setting value candidates.

6. The fluorescent X-ray analysis method according to claim 3, further comprising:
    evaluating the reliability of measurement from the outputted measured concentration and the measurement accuracy, wherein a comparison is made with threshold values set for the measured concentration and for the measurement accuracy, and the outputted measured concentration and measurement accuracy are ranked on a scale.

7. The fluorescent X-ray analysis method according to claim 6, wherein the evaluating involves combining the rankings for measured concentration and measurement accuracy and performing a final evaluation.

8. The fluorescent X-ray analysis method according to claim 6, wherein the setting involves setting the threshold values.

9. A fluorescent X-ray analysis device in which the constituent elements of a sample are analyzed from the fluorescent X-rays emitted when the sample is irradiated with X-rays, comprising:
an input unit for inputting the setting of the sample measurement condition;
an irradiation control unit for controlling X-ray irradiation according to the measurement condition;
a detection unit for detecting the fluorescent X-rays;
a computation unit for computing the measured concentration and measurement accuracy on the basis of signals from the detection unit:
an output unit for outputting the computation result; and
a control unit for terminating the measurement of fluorescent X-rays when the measurement accuracy computed by the computation unit satisfies the measurement condition, wherein
the measurement condition is that the measurement accuracy drops below a predetermined setting value,
the setting value is obtained by dividing the measured concentration by a predetermined value.

10. A fluorescent X-ray analysis device in which the constituent elements of a sample are analyzed from the fluorescent X-rays emitted when the sample is irradiated with X-rays, comprising:
an input unit for inputting the setting of the sample measurement condition;
an irradiation control unit for controlling X-ray irradiation according to the measurement condition;
a detection unit for detecting the fluorescent X-rays;
a computation unit for computing the measured concentration and measurement accuracy on the basis of signals from the detection unit;
an output unit for outputting the computation result; and
a control unit for terminating the measurement of fluorescent X-rays when the measurement accuracy computed by the computation unit satisfies the measurement condition, wherein
the measurement condition is that the measurement accuracy drops below a calculation value obtained by dividing the measured concentration by a predetermined value when the calculation value is larger than a setting value, or that the measurement accuracy drops below the calculation value when the calculation value is smaller than the setting value.

11. The fluorescent X-ray analysis method according to claim 10, wherein the setting value is obtained by dividing the upper limit target value for variance in the measured concentration by an accuracy coefficient that expresses the desired level of accuracy in measurement.

12. A fluorescent X-ray analysis device in which the constituent elements of a sample are analyzed from the fluorescent X-rays emitted when the sample is irradiated with X-rays comprising:
an input unit for inputting the setting of the sample measurement condition;
an irradiation control unit for controlling X-ray irradiation according to the measurement condition;
a detection unit for detecting the fluorescent X-rays;
a computation unit for computing the measured concentration and measurement accuracy on the basis of signals from the detection unit;
an output unit for outputting the computation result; and
a control unit for terminating the measurement of fluorescent X-rays when the measurement accuracy computed by the computation unit satisfies the measurement condition, wherein
the measurement condition is that the measurement accuracy drops below a predetermined setting value,
the setting value is obtained by dividing the upper limit target value for variance in the measured concentration by an accuracy coefficient that expresses the desired level of accuracy in measurement.

13. A fluorescent X-ray analysis method in which the constituent elements of a sample are analyzed from the fluorescent X-rays emitted when the sample is irradiated with X-rays comprising:
setting a sample measurement condition;
measuring the fluorescent X-rays;
deriving the measured concentration and measurement accuracy of the constituent elements from the results of the measurement;
terminating the measurement of the fluorescent X-rays when the measurement accuracy satisfies the measurement condition; and
outputting the measured concentration or measurement accuracy, wherein
the measurement condition is that the measurement accuracy drops below a predetermined setting value,
the setting value is obtained by dividing the upper limit target value for variance in the measured concentration by an accuracy coefficient that expresses the desired level of accuracy in measurement.

14. The fluorescent X-ray analysis method according to claim 13, wherein the setting involves inputting at least one of the upper limit target value and the accuracy coefficient.

15. The fluorescent X-ray analysis method according to claim 13, wherein the setting involves inputting at least one of the upper limit target value for a plurality of different values and a plurality of the accuracy coefficients corresponding to the various upper limit target values, deriving a plurality of setting value candidates for each of the upper limit target values or accuracy coefficients, and deciding on one of the setting values from the derived plurality of setting value candidates.

16. The fluorescent X-ray analysis method according to claim 13, further compnsing:
evaluating the reliability of measurement from the outputted measured concentration and the measurement accuracy, wherein a comparison is made with threshold values set for the measured concentration and for the measurement accuracy, and the outputted measured concentration and measurement accuracy are ranked on a scale.

17. The fluorescent X-ray analysis method according to claim 16, wherein the evaluating involves combining the rankings for measured concentration and measurement accuracy and performing a final evaluation.

18. The fluorescent X-ray analysis method according to claim 16, wherein the setting involves setting the threshold values.

* * * * *

UNITED STATES PATENT AND TRADEMARK OFFICE
Certificate

Patent No. 7,382,855 B2                          Patented: June 3, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Yoshiyuki Tani, Osaka (JP); Hiroshi Iwamoto, Osaka (JP); Takao Hisazumi, Osaka (JP); Yukihiro Iwata, Osaka (JP); Etsuyoshi Sakaguchi, Osaka (JP); and Kiyoshi Hasegawa, Chiba (JP).

Signed and Sealed this Fourteenth Day of August 2012.

MINH-TOAN TON
*Supervisory Patent Examiner*
Art Unit 2882
Technology Center 2800